United States Patent
Faini et al.

(10) Patent No.: US 11,877,799 B2
(45) Date of Patent: Jan. 23, 2024

(54) OPTICAL COHERENCE TOMOGRAPHY SYSTEM OF THE "FOURIER-DOMAIN" TYPE WITH REMOVAL OF UNDESIRED ARTIFACTS THROUGH DIGITAL IMAGE PROCESSING

(71) Applicant: COSTRUZIONI STRUMENTI OFTALMICI C.S.O. S.R.L., Scandicci (IT)

(72) Inventors: Stefano Faini, Florence (IT); Lorenzo Rosellini, Campi Bisenzio (IT); Francesco Versaci, Prato (IT); Gabriele Vestri, Florence (IT)

(73) Assignee: COSTRUZIONI STRUMENTI OFTALMICI C.S.O. S.R.L., Scandicci (IT)

( * ) Notice: Subject to any disclaimer, the term of this patent is extended or adjusted under 35 U.S.C. 154(b) by 434 days.

(21) Appl. No.: 17/258,904

(22) PCT Filed: Jul. 30, 2019

(86) PCT No.: PCT/IB2019/056487
§ 371 (c)(1),
(2) Date: Jan. 8, 2021

(87) PCT Pub. No.: WO2020/026138
PCT Pub. Date: Feb. 6, 2020

(65) Prior Publication Data
US 2021/0290052 A1    Sep. 23, 2021

(30) Foreign Application Priority Data
Aug. 1, 2018   (IT) ........................ 102018000007723

(51) Int. Cl.
*A61B 3/10*    (2006.01)
*G06T 7/269*   (2017.01)
(Continued)

(52) U.S. Cl.
CPC ............ *A61B 3/102* (2013.01); *A61B 5/7207* (2013.01); *G01B 9/02044* (2013.01);
(Continued)

(58) Field of Classification Search
CPC .. A61B 3/102; A61B 5/7207; G01B 9/02044; G01B 9/02091; G06T 7/269;
(Continued)

(56) References Cited

U.S. PATENT DOCUMENTS 9,167,964 B2 * 10/2015 Everett ................ A61B 5/0066
2013/0010259 A1 * 1/2013 Carnevale ............ A61B 3/102
                                                              351/209
(Continued)

FOREIGN PATENT DOCUMENTS

WO    2010117386 A1    10/2010

OTHER PUBLICATIONS

Bernd Hofer, et al., "Dispersion Encoded Full Range Frequency Domain Optical Coherence Tomography", Optics Express, vol. 17, No. 1, pp. 7-24, 2009.
Yuankai K. Tao, et al., "High-Speed Complex Conjugate Resolved Retinal Spectral Domain . . . ", Optics Letters, vol. 32, No. 20, pp. 2918-2920, 2007.

(Continued)

*Primary Examiner* — Siamak Harandi
*Assistant Examiner* — Daniella M. DiGuglielmo
(74) *Attorney, Agent, or Firm* — Lucas & Mercanti, LLP

(57) ABSTRACT

The present invention relates to the field of instruments for visualizing the inner structures of the human body, and in particular of the eye. More specifically, its object is an optical coherence tomography system and method of the "Fourier-domain" type with the removal of unwanted artifacts through digital image processing.

10 Claims, 8 Drawing Sheets

(51) Int. Cl.
*A61B 5/00* (2006.01)
*G01B 9/02091* (2022.01)
*G06T 11/00* (2006.01)
*G01B 9/02* (2022.01)

(52) U.S. Cl.
CPC .......... *G01B 9/02091* (2013.01); *G06T 7/269* (2017.01); *G06T 11/005* (2013.01); *G06T 11/008* (2013.01); *G06T 2207/10101* (2013.01); *G06T 2207/20021* (2013.01); *G06T 2210/41* (2013.01)

(58) Field of Classification Search
CPC ................ G06T 11/005; G06T 11/008; G06T 2207/10101; G06T 2207/20021; G06T 2210/41
See application file for complete search history.

(56) References Cited

U.S. PATENT DOCUMENTS

| | | | |
|---|---|---|---|
| 2013/0044330 A1* | 2/2013 | Kang | G01B 9/02091 356/479 |
| 2013/0088721 A1* | 4/2013 | Yang | G01B 9/02083 356/479 |
| 2017/0119247 A1* | 5/2017 | Walsh | A61B 3/0041 |

OTHER PUBLICATIONS

International Search Report and Written Opinion for Corresponding International Application No. PCT/IB2019/056487 (9 Pages) (dated Oct. 24, 2019).

\* cited by examiner

OPTICAL COHERENCE TOMOGRAPHY SYSTEM OF THE "FOURIER-DOMAIN" TYPE WITH REMOVAL OF UNDESIRED ARTIFACTS THROUGH DIGITAL IMAGE PROCESSING

CROSS-REFERENCE TO RELATED APPLICATIONS

This application is a 371 of PCT/IB2019/056487, filed Jul. 30, 2019, which claims the benefit of Italian Patent Application No. 102018000007723, filed Aug. 1, 2018.

FIELD OF THE INVENTION

The present invention relates to the field of instruments for visualizing the inner structures of the human body, and in particular of the eye. More specifically, it concerns an optical coherence tomography system of the "Fourier-domain" type with the removal of undesired artifacts through digital image processing.

BACKGROUND OF THE INVENTION

Optical coherence tomography (OCT), also called phase optical coherence tomography, is one of the most powerful and most developed biomedical imaging techniques. It finds application in various fields of medicine. The ophthalmological sector has certainly contributed to its development and improvement.

In this technique, information on the structure of the observed sample/organ is derived from the back-reflected and/or backscattered radiation from regions that show different optical properties within the sample/organ itself.

The OCT technique allows creating two-dimensional or three-dimensional models with a resolution ranging from one to a few μm. In addition to allowing morphological study, OCT can reveal other biological properties of the analysed sample, such as for example the speed of a flow (through the Doppler effect) and birefringence (through polarization changes).

OCT finds its basis in low coherence interferometry. The optical set-up of an OCT system is based on a Michelson interferometer, and the operating mode of the OCT system is determined depending on the type of radiation source and detection method used. At present, there are two main arrangements that are used in OCT instruments.

The reflectivity profile of the sample is obtained through interference of the radiation coming from an optical arm of the sample with that coming from an optical reference arm whose path is modified in a determined time interval. The resulting interferogram pattern provides information on the position and dispersion amplitude of the diffusive elements in the sample.

In so-called Time-Domain OCT (TD-OCT), this information is typically extracted by scanning the delay of the reference optical arm and detecting the interferogram as a function of this delay. The envelope of the detected interferogram represents a map of the reflectivity of the sample in relation to its depth, commonly called A-scan, with the depth resolution given by the coherence length of the source. A plurality of A-scans is acquired while the sample beam is scanned laterally across the surface of the tissue, constructing a two-dimensional map of reflectivity in relation to depth and lateral extension, called B-scan.

Fourier Domain OCT (FD-OCT) instead records in a single step, without requiring a mechanical translation of elements in the reference arm, the spectral fringes caused by the recombination of the radiation coming from the arm of the sample with that coming from the reference arm, in a wide spectral band. The measurement of the distances of the various elements of the sample is obtained by processing the interferogram signal. Since the A-scan data is collected in parallel, this second technique is much faster than the first, where destructive recombination is typically used to isolate the interferometric signal one depth at a time, while the reference delay is scanned. It also has benefits in terms of signal to noise ratio that result in higher image quality.

The second FD-OCT technique can in turn be applied according to two main implementation schemes:
  in Spectral Domain OCT (SD-OCT) the spectrum is obtained using a broadband radiation source and a spectrometer that measures its intensity with a linear sensor (line-scan camera);
  in Swept Source OCT (SS-OCT) the spectrum is obtained from a single radiation detector by varying the wavelength emitted by the source at very high speeds.

To further illustrate these concepts by way of example, with specific reference to FIG. 1, which refers to a traditional SD-OCT configuration, the system provides:
  a broadband radiation source LBS;
  a reference optical arm RA that contains a collimation system RAFC and a mirror MRef;
  a sample arm SA containing a scanning system, consisting of a collimation system SAFC, mirrors and actuators M, and a lens L1, which allows illuminating a strip (in the axial direction) of the sample for which an image is to be created, and collecting its backscattered radiation;
  a signal detection arm MA with a spectrometer Spec that allows analysing the spectrum of the signal resulting from the recombination of the radiation collected by the reference arm RA and the sample arm SA, comprising a linear sensor that reveals the signal spectrum of interference corresponding to the illuminated sample strip;
  a beam splitter BS configured to allow the passage of radiation from the source LBS to the sample arm SA and the reference arm RA, and from these to the detection arm MA; and
  a control and processing unit CPU which suitably drives the mechanical and electronic parts and which derives from the spectrum, through one of the many algorithms known in literature, the reflectivity profile of the strip of the sample for which an image is to be produced.

The radiation from the broadband source LBS is transmitted to the reference arm RA and the sample arm SA in front of which the sample to be displayed is placed. The radiation in the reference arm RA is reflected by the mirror MRef and is sent through the beam splitter BS to the detection arm MA. Similarly, the radiation in the sample arm SA is backscattered by the illuminated portion of the sample and reaches the detection arm MA through the beam splitter BS. Then the two light waves coming from the reference arm RA and the sample arm SA, recombine on the detection arm MA where the spectrometer Spec reconstructs the spectrum of the interference signal (interferogram) on a linear sensor.

In both the SD-OCT and SS-OCT configurations, the radiation returned by each depth is, as mentioned, collected simultaneously, and is shown as modulations in the detected spectrum. The transformation of the detected spectrum from wavelength to wave number, the correction of dispersive mismatches between the sample arm and the reference arm, and the fast Fourier transformation typically provide the A-scan which directly represents the reflectivity of the sample resolved in depth.

This A-scan can however present complex conjugate artifacts, i.e. the presence of mirror images in the reconstructed image (as seen in FIG. 4, noting the arch-shaped mark in the upper region of the image). These are due to the fact that the detected spectral interferogram is a real function, whose Fourier transform typically has Hermitian symmetry (i.e. positive and negative spatial frequencies are not independent). Consequently, reflections of the sample at a positive displacement, relative to the reference delay, cannot be distinguished from reflections at the same negative displacement, and appear as inverted images superimposed on the true structure of the sample. Therefore, the reconstructed image appears to contain two symmetrical imprints with respect to the null path difference.

These issues may be of little relevance when it comes to observing objects distributed in a thin spatial range (for example the retinal layers), because it is possible to move the reference arm to a position where the mirrored image does not overlap the sample image to be acquired, in practice by performing the acquisition so that the entire sample is positioned either above or below the reference position, which is possible only with thin samples.

On the contrary, if objects with greater depth must be measured and for which the entire measurement range is needed (for example the anterior segment of the eye), the artifacts significantly worsen the quality of the image and make it difficult to interpret the data collected. Furthermore, the sensitivity loss of the FD-OCT technique with the distance from the zero position would make a differentiation between positive and negative distances valuable, especially in the SD-OCT field area, because this would allow positioning the object in the measurement field where sensitivity is higher, i.e. directly near the corresponding zero position.

It has been proposed to solve this problem by measuring the phase of the spectral interferometric signal, thus providing access to the complex optical diffusion field [Fercher et al. "Complex spectral interferometry OCT"—Proc. SPIE. 1999:3564: 173-178]. According to this approach (FRC—full range complex), an inverse Fourier transform of complex data provides the real structure of the object, eliminating any specular terms. Also on this basis, various proposals have been made using methods that require a certain number of A-scans at a given sampling position, changing the reference phase between them by means of acoustic-/electro-optical phase modulators or piezoelectric control mirrors. Among the most recent, the following can be mentioned: Wojtkowski et al. "Full range complex spectral optical coherence tomography technique in eye imaging"—Opt. Lett. 2002; 27:1415-1417, Targowski P et al. "Complex spectral OCT in human eye imaging in vivo"—Opt. Commun. 2004; 229:79-84, Leitgeb R A et al "Phase shifting algorithm to achieve high speed long depth range probing by frequency domain optical coherence tomography"—Opt. Lett. 2003; 28:2201-2003, Götzinger E et al. "High speed full range complex spectral domain optical coherence tomography"—Opt. Express. 2005; 13:583-594, e Bachmann A et al. "Heterodyne Fourier domain optical coherence tomography for full range probing with high axial resolution"—Opt. Express. 2006; 14:1487-1496.

The drawbacks of these techniques lie in the need to adopt additional components and to reduce the measurement speed due to the multiple A-scans.

Another FRC FD-OCT scheme uses a linearly increasing phase shift, generated by a uniform motion of a piezoelectrically controlled reference mirror during a B-scan [Yasuno Y et al. "Simultaneous B-M-mode scanning method for real-time full-range Fourier domain optical coherence tomography"—Appl. Opt. 2006; 45:1861-1865, Wang R K "In vivo full range complex Fourier domain optical coherence tomography"—Appl. Phys. Lett. 2007; 90:054103]. The complex data are obtained from a combination of Fourier transforms and Hilbert transforms in the transverse direction. This method (which can in turn also be implemented with acoustic-/electro-optical phase modulators) has the advantage of requiring only a single A-scan per measurement position, so that the acquisition speed is certainly increased. However, a structural complication remains due to the additional element (and relative drives) for the phase shift.

A further technique that has been proposed [Yasuno Y et al. "Simultaneous BM-mode scanning method for real-time full-range Fourier domain optical coherence tomography"—Appl. Opt. 2006; 45:1861-1865; Wang R K "In vivo full range complex Fourier domain optical coherence tomography"—Appl. Phys. Lett. 2007; 90:054103] avoids the additional element for the phase shift, which can be obtained through the galvanometric scanner used for the transverse scanning of the sample beam.

SUMMARY OF THE INVENTION

The object of the present invention is to provide an FD-OCT system for the removal of the above-described artifacts which allows offering a conceptually different solution to those already known, with prerogatives that surprisingly combine detection accuracy and speed, structural simplicity, flexibility and integration possibilities with multi-resolution strategies in order to further increase the final accuracy of the result.

This and other objects are achieved with the "Fourier-domain" optical coherence tomography system with the removal of undesired artifacts through digital image processing according to the present invention, whose essential characteristics are defined by the first of the appended claims. Further important implementation features are defined by the dependent claims.

The invention therefore envisages removing the artifacts by resorting to motion estimations with digital image processing. The proposed system envisages using an OCT device to acquire a temporal sequence of tomographic images, processing this sequence using motion estimation techniques in order to identify and remove the graphic features related to the undesired specular artifacts, which are identified thanks to the fact that they have an opposite axial movement component with respect to the graphic features of the real images. Several estimation techniques suitable for this purpose are proposed and can be used, none of which limit the invention. The aforementioned techniques can also be used as an alternative, but also combined with each other to provide an even more refined result, depending on the available computing resources and/or the pre-set quality objectives, and/or a compromise that from time to time appears to be optimal based on accessory conditions which are subjected or imposed. In this sense, i.e. in relation to the selection and application choices of motion estimation techniques, the proposed system also offers the advantage of high modularity/flexibility, as well as the possibility of marked integration with multi-resolution strategies.

The resolution of the artifacts according to the invention, ultimately, effectively improves the image acquisition process, and allows the operator to position the most critical region of the sample at the position with the most favourable signal to noise ratio.

BRIEF DESCRIPTION OF THE DRAWINGS

The characteristics and advantages of the "Fourier-domain" optical coherence tomography system with the removal of undesired artifacts through digital image processing according to the present invention will become clearer from the following description of an embodiment thereof, made by way of non-limiting example, with reference to the annexed drawings in which.

DETAILED DESCRIPTION OF THE INVENTION

Figure 1:
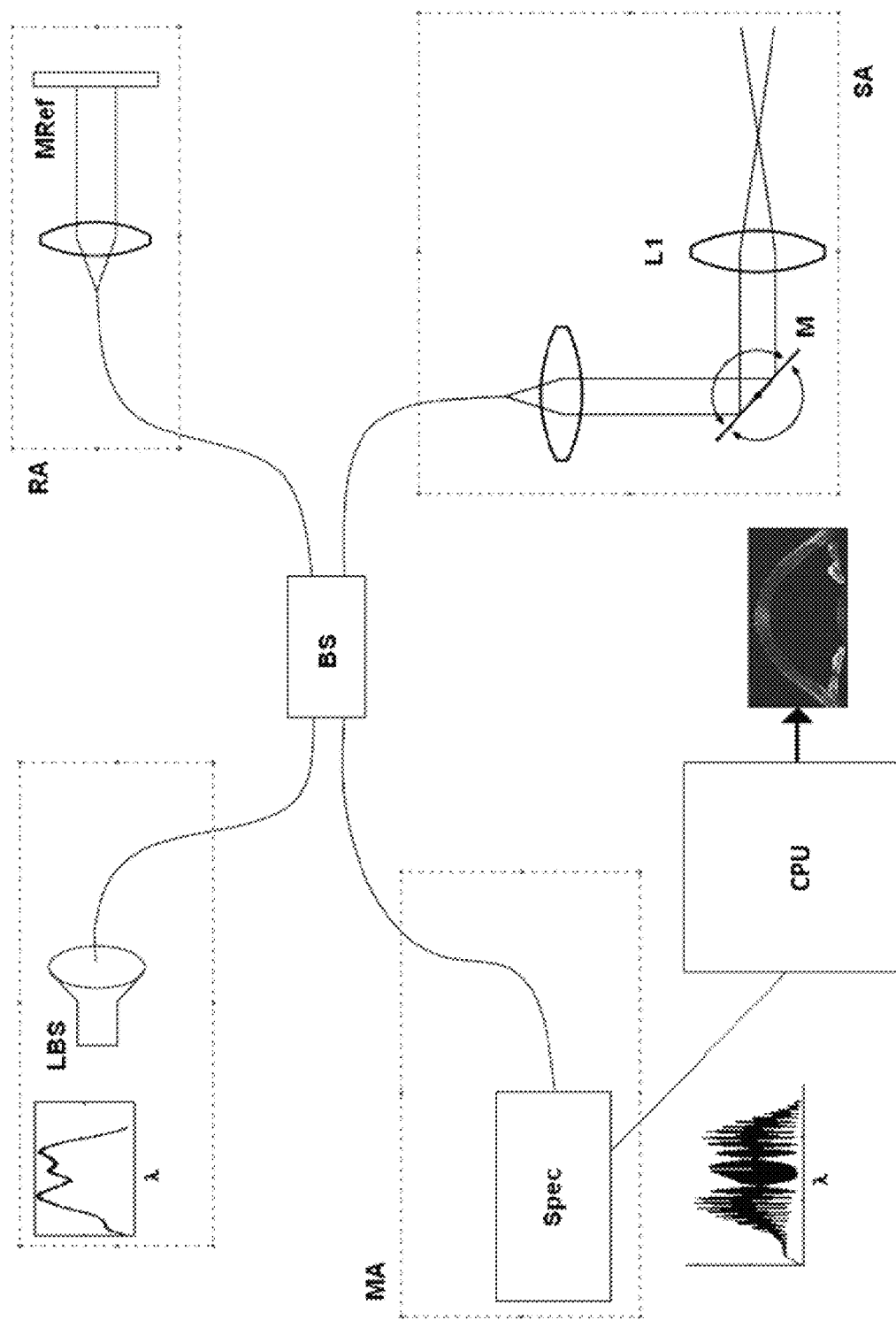
FIG. 1 is a diagram representing a traditional SD-OCT configuration.
Figure 2:
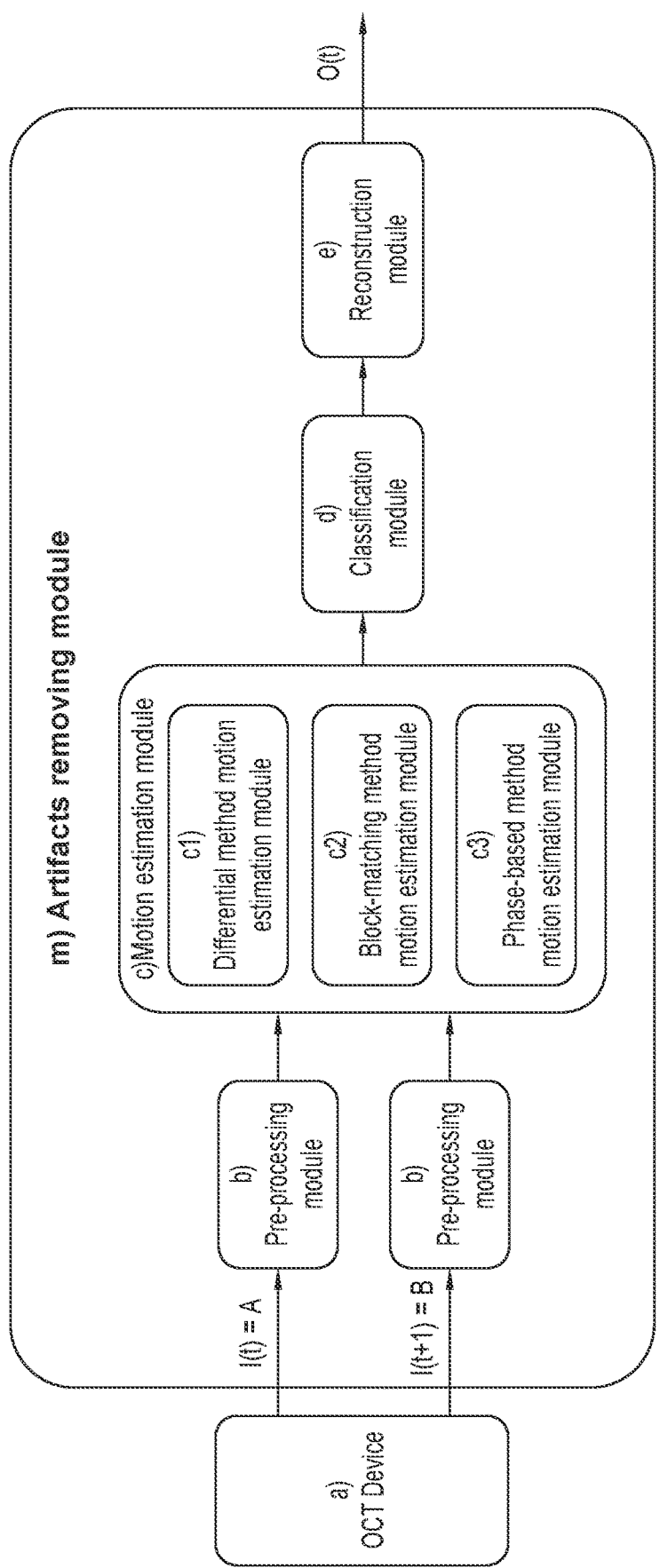
FIG. 2 is a global architectural diagram of the system according to a possible embodiment of the present invention.
Figure 4:
FIG. 4 is an image A relating to a tomographic section of an eye acquired at a time t.
Figure 5:
FIG. 5 is an image B relating to a tomographic section of an eye acquired at a time t+1.

With reference to the aforementioned figures, and in particular for the moment to FIG. 2, in the context of the present invention the mirror artifact removal system present within a sequence of temporally consecutive images acquired with the FD-OCT device is based on a motion estimation module c), which according to the fundamental aspect of the invention was chosen in order to identify and remove artifacts; in other words, a calculation of the optical flow present within a sequence of temporally consecutive tomographic images is performed (see FIGS. 4 and 5). The calculated optical flow is then used to identify and subsequently remove the mirror components present in the sequence itself.

The term "optical flow" defines a vector field resulting from the application of one or more motion estimation methods whose elements are vectors that describe the displacements to which the individual elements present are subjected (brightness pattern), within a sequence of temporally consecutive tomographic images. An element is defined in terms of its support region, i.e. the set of pixels to which a specific motion model is applied. The displacements are estimated in terms of space-time variations of the light intensity values associated with these elements.

The estimation module can in practice resort to different embodiments, all falling within the scope of the present invention and which in themselves rely on known knowledge, it being understood that it is not precisely the estimation technique in itself that represents the invention, but its unprecedented use in the present context and for the specific result. Different modules structured according to different techniques therefore define different embodiments of the invention.

The proposed system is therefore not restricted by the application of a specific motion estimation method; different methods can be applied individually or jointly depending on specific constraints including the computational resources available and the desired estimation quality. In order to carry out the invention with a reduction to practice, specific implementations of such methods are ultimately used, carried out and adapted in order to optimize the estimation of the optical flow in the presence of sequences of tomographic images acquired with OCT devices.

The methods for motion estimations for which theoretical bases are offered in literature comprise:

Approaches based on differential methods of optical flow resolution: these methods estimate the motions by solving the optical flow equation together with further motion uniformity equations. Examples of developing the uniformity constraint are shown in the following articles:

Horn et al. "Determining optical flow."—*Artificial intelligence* 17.1-3 (1981): 185-203.

Lucas, Bruce D. et al. "An iterative image registration technique with an application to stereo vision."—DARPA Image Understanding Workshop, 1981: pp. 121-130. [1]

Pel-Recursive type approaches: these methods recursively estimate the displacements by minimizing a functional defined as DFD (Displaced Frame Difference); the image is generally scanned in raster mode, implementing the recursion on a pixel basis. An example of this approach is reported in Netravali et al. "Motion-Compensated Television Coding: Part I."—*Bell Labs Technical Journal* 58.3 (1979): 631-670.

Block-Matching type approaches: the methods attributable to this type of approach subdivide the images into blocks and carry out similarity measurements between them within the temporal sequence of the same. The purpose of these methods is to maximize these similarity measurements within a given searched spatial window. In this case the motion uniformity constraint is implicitly defined within the analysed block with a level proportional to the size of the block itself. In order to optimize execution times, these methods are implemented by adopting different search strategies and matching criteria. An example of such an approach is reported in Zhu, Ce et al. "Hexagon-based search pattern for fast block motion estimation."—*IEEE transactions on circuits and systems for video technology* 12.5 (2002): 349-355. [2]

Approaches based on the transform domain: the basic criterion of these methods consists in carrying out the estimation of the motion vectors by exploiting features associated with them in the domain of the Fourier or wavelet transforms.

Examples of such approaches are reported in:
Haskell, B. "Frame-to-frame coding of television pictures using two-dimensional Fourier transforms (Corresp.)."—*IEEE Transactions on Information Theory* 20.1 (1974): 119-120.
Fleet, David J. et al. "Computation of component image velocity from local phase information."—*International journal of computer vision* 5.1 (1990): 77-104. [3]

Other presentations that contain elements that can be used for implementation purposes are reported in the following articles:
Barron, John L., David J. Fleet, and Steven S. Beauchemin. "Performance of optical flow techniques." *International journal of computer vision* 12.1 (1994): 43-77.
Galvin, Ben, et al. "Recovering Motion Fields: An Evaluation of Eight Optical Flow Algorithms." *BMVC. Vol.* 98. 1998.
McCane, Brendan, Ben Galvin, and Kevin Novins. "On the evaluation of optical flow algorithms." *Fifth International Conference on Control, Automation, Robotics and Vision, Singapore.* 1998.

With regard to synthetic and generic images, the methods for calculating optical flow which have highlighted better results in terms of estimation error are those of the differential and phase-based type in the implementations proposed by the aforementioned:
Lucas, Bruce D. et al. "An iterative image registration technique with an application to stereo vision."—DARPA Image Understanding Workshop, 1981: pp. 121-130. [1]
Fleet, David J. et al. "Computation of component image velocity from local phase information."—*International journal of computer vision* 5.1 (1990): 77-104. [3]

All the above having been stated, and referring specifically to the diagram shown in FIG. 2, the proposed system therefore comprises:
An FD-OCT acquisition device a);
A block m) for the removal of mirror artifacts, in turn comprising in sequence:
At least one pre-processing module b);
The aforementioned motion estimation module c), which on the basis of the chosen technique can be materialized by a module c1), c2), c3) . . . cn) or a combination thereof;
A classification module d); and
A reconstruction module e).

The term "module" can be intended as a pure software implementation or as a combination of hardware and software features, in any case allocated in a physical control and processing unit, with architecture and performance drawn from the technological landscape/market available to the expert in the field. The execution and storage of the instructions relating to the implemented software procedures is not restricted to specific hardware architectures, such that they may be carried out inside a generic computer or on specific PCBs for digital signal processing. The program code for the creation of the instructions contained in each processing module can be implemented through the use of procedural languages such as C and also object-oriented languages such as C++, C #, Java.

On the other hand, the program code relating to a specific module, in the absence of specific hardware restrictions, can be carried out: entirely in the local processing device, partially in the local processing device, partially in a remote processing device or entirely in a remote processing device. In these last two scenarios the connections can be made through Local Area Network (LAN) or Wide Area Network (WAN) technologies.

Figure 3:
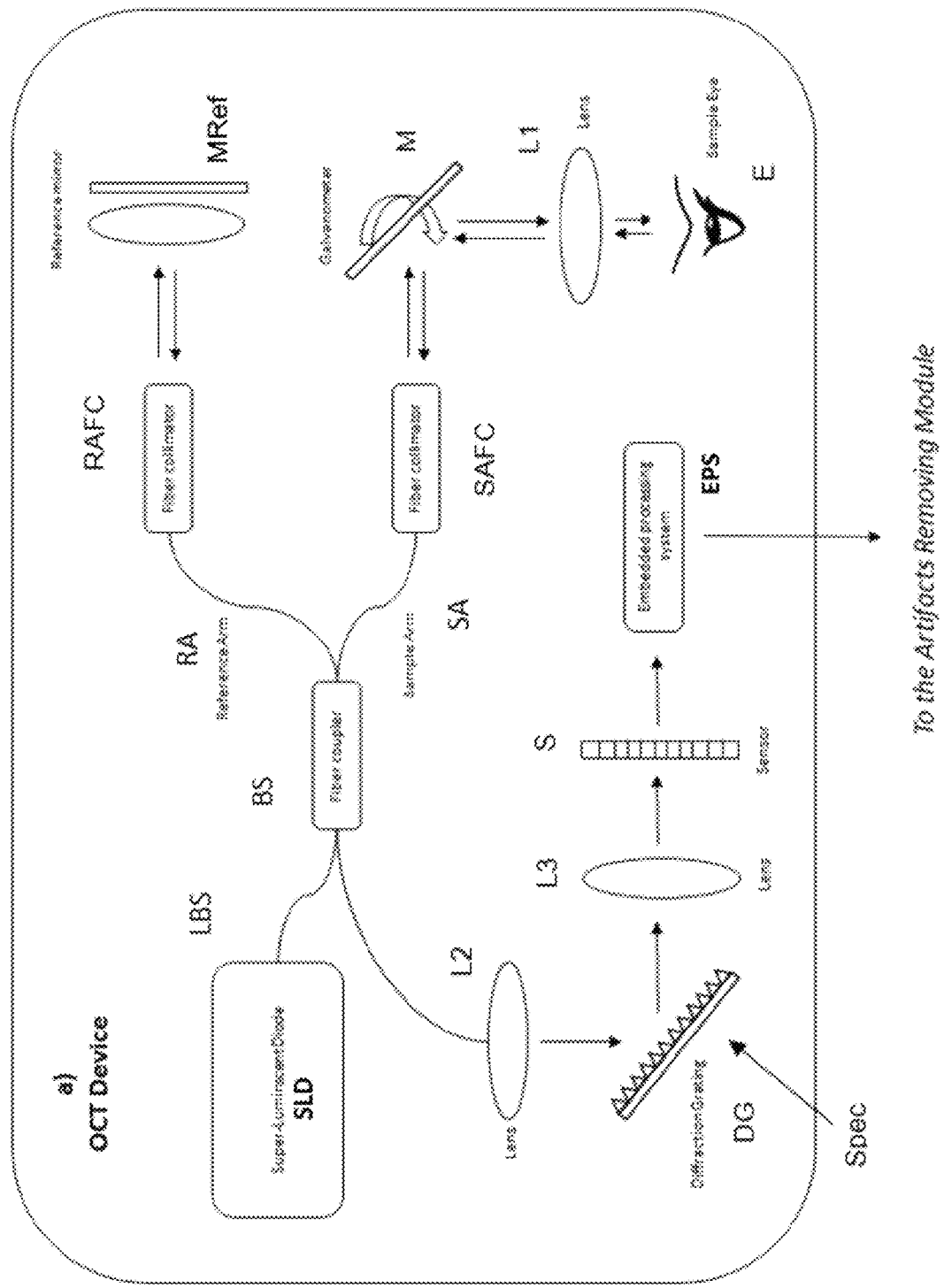
FIG. 3 is a generic architectural diagram of an FD-OCT device based on a spectrometer used in the context of the aforementioned embodiment of the invention.

Going even more in detail from the implementation point of view, the architecture then taken as an example for the diagram of FIG. 3, specifically concerning the acquisition device a), envisages using a spectrometer-based SD-OCT optical coherence technology, but this does not limit the application of the present invention, which can extend, according to what is obviously understandable (or adaptable) to a person skilled in the art, to other types of known solutions, for example and in particular SS-OCT.

In the specific implementation the device a) will thus provide a superluminescent broadband diode SLD as the LBS source. The light beam emitted is divided through a splitter BS into two distinct paths: a path on the reference arm RA and a path on the sample arm SA. The path through the sample arm SA, comprising collimation means SAFC, is suitably directed through one or more galvanometrically actuated mirrors M, along certain scan axes and with the aid of a lens L1, towards the sample in question E. The reference arm RA in turn comprises collimation means RAFC and a reference mirror MRef.

Exploiting the principles of interferometry, the return light beam caused by the backscattering of the sample interfaces E (eye to be measured) is then combined together with the light beam coming from the reference arm RA and sent to the spectrometer Spec detection arm MA. The main elements of the spectrometer component, beyond a lens system L2, L3, consist in a diffraction grating DG, capable of separating the light beam in its individual wave components, and a sensor S of the linear CCD type, able to receive these components and transform them into an appropriate electrical signal. The signal produced by the linear sensor S consists of an interferogram dependent on the type of surface analysed and containing the continuous, auto-correlation and cross-correlation components deriving from the interference phenomena; the reconstruction of the tomographic images in the spatial domain takes place, inside an integrated processing block EPS, operating a Fourier transform of the signal itself.

The sequence of tomographic images thus obtained is then transmitted, according to the invention, to the block m) for removing the artifacts. In the latter, a pre-processing module b) is adapted to carry out filtering operations aimed at increasing the signal to noise ratio by reducing the speckle noise component intrinsically present within the images acquired with OCT technology. The filtering algorithms chosen and the corresponding parameters of use will be such as to allow an adequate reduction of the noise component, adequately preserving the signal features subsequently used for the calculation of the optical flow. A filtering that can be used is for example the adaptive type reported in: Jong-Sen Lee, "Digital Image Enhancement and Noise Filtering by Use of Local Statistics"—*IEEE Transac. On Pattern Analysis and Machine Intelligence*, Vol. PAMI-2, No. 2, 1980, pp. 165-168.

In the most prominent aspect of the present invention, the images therefore undergo processing by the module c), which contains the logic for estimating the optical flow and the subsequent classification of the image regions. As already mentioned, this estimation can be derived from the use of the single method or from an analysis of the information deriving from a combination of them. The combined use of the aforementioned optical flow estimation methods allows the implementation of outlier rejection strategies outside the context of the specific method, improving the reliability of the estimation itself.

In the following, three implementation hypotheses c1), c2), c3) will be analytically described, based on some of the methodological approaches mentioned above.

c1) Motion Estimation Module with the Differential Method

In this embodiment, the algorithm described in the publication [1] cited above is taken as a basic reference. One embodiment of the specifically optimized method in the context of the present invention is articulated through the following steps.

First, a list of representative image points L{p} is created with respect to which the corresponding optical flow vectors will be subsequently calculated. The criterion for choosing the representative points can take place with a constant sampling step or with a variable sampling step and chosen as a function of local features of the image considered discriminating for the purposes of the subsequent calculations.

Then the calculation of the two pyramids is carried out, each of which with n levels containing multi-resolution representations of two images A and B deriving from temporally consecutive acquisitions $A:\{A^L\}_{L=0 \ldots L_n}$ $B:\{B^L\}_{L=0 \ldots L_n}$. The single image contained at the level $L_i$ is calculated through a low-pass and scaling filtering operation of the corresponding image at the level $L_{i-1}$, this representation is such that the value at n corresponds to the minimum resolution image while at the level 0 the image corresponds to the maximum resolution.

For each representative image point p contained in the list L{p} the algorithm for estimating the optical flow vector is applied by iterating through each level of the pyramid. Starting from the lower resolution level the calculated estimations are propagated to the next higher level of the pyramid and used as an initial value for the refinement of the estimation. The optical flow relative to a representative point is calculated by imposing the motion uniformity constraint near the point itself; this constraint is formalized by setting the following system of linear equations:

$$A_x(q_1)r_x + A_y(q_1)r_y = -A_t(q_1)$$

$$A_x(q_2)r_x + A_y(q_2)r_y = -A_t(q_2)$$

$$\sim\sim\sim\sim$$

$$A_x(q_n)r_x + A_y(q_n)r_y = -A_t(q_n)$$

where:

$q_1, q_2, \ldots q_n$: are the points near the representative point of interest for which the motion uniformity constraint is imposed $A_x(q_1)$, $A_y(q_1)$: are the partial derivatives with respect to the spatial coordinates calculated in the neighbouring points mentioned above $r_x$, $r_y$: are the components of the unknown speed vector associated with the representative point of interest $A_t(q_i)$: are the partial derivatives with respect to the time calculated in the neighbouring points mentioned above The linear system reported above is solved by the least squares regression.

If $p_L = [p_x, p_y]$ is the position of the representative point within the layer image calculated as $p/2^L$ in reference to the position taken at maximum resolution and $$A_x^L(x, y) = \frac{A^L(x+1, y) - A^L(x-1, y)}{2}$$

$$A_y^L(x, y) = \frac{A^L(x, y+1) - A^L(x, y-1)}{2}$$

are the partial derivatives at level L, the least-squares resolution of the above problem generates the spatial gradient matrix $$G = \sum_{x=p_x-r_x}^{p_x-r_x} \sum_{y=p_y-r_y}^{p_y+r_y} \begin{bmatrix} A_x^L(x, y)A_x^L(x, y) & A_x^L(x, y)A_y^L(x, y) \\ A_x^L(x, y)A_y^L(x, y) & A_y^L(x, y)A_y^L(x, y) \end{bmatrix}$$

and the correspondence error vector $$b = \sum_{x=p_x-r_x}^{p_x+r_x} \sum_{y=p_y-r_y}^{p_y+r_y} \begin{bmatrix} A_t(x, y)A_x^L(x, y) \\ A_t(x, y)A_y^L(x, y) \end{bmatrix}$$

The following system of linear equations is then solved with the Newton-Raphson method through the spatial gradient matrix and the correspondence error vector.

$$v = \begin{bmatrix} l_x' \\ l_y' \end{bmatrix} = G^{-1}b$$

A pseudo-code representation of the method used is also shown here below.

If p is a representative point in the context of image A, find the corresponding position q in the context of image B.
Construction of a multi-resolution pyramidal representation of images A and B:

$$A:\{A^L\}_{L=0 \ldots L_n} B:\{B^L\}_{L=0 \ldots L_n}$$

Initialization of initial estimation relative to the minimum resolution level $g^{L_n} = [g_x^{L_n}, g_y^{L_n}] = [0,0]$
Proceed from $L=L_m$ up to $L=0$ with step 1:
   Position of the point p on image $A^L: p^L = [p_x, p_y] = p/2^L$
   Image derivative calculation $A_x^L(x,y)$ $A_y^L(x,y)$
   Spatial gradient matrix calculation G
   Speed estimation initialization $v^0 = [0,0]$
   Proceed from k=1 up to $K_{max}$ or until $\|\mu^k\| < th$
   Image difference calculation:

$$\delta A_k(x,y) = A_L(x,y) - B^L(x + g_x^L + v_x^{k-1}, y + g_y^L + v_y^{k-1})$$

Correspondence error vector calculation:

$$b_k = \sum_{x=p_x-r_x}^{p_x+r_x} \sum_{y=p_y-r_y}^{p_y+r_y} \begin{bmatrix} \delta A_k(x, y)A_x^L(x, y) \\ \delta A_k(x, y)A_y^L(x, y) \end{bmatrix}$$

Optical flow vector calculation: $\mu^k = G^{-1}b_k$
   Estimation update: $v^k = v^{k-1} + \mu^k$
End of cycle on k
Final optical flow vector at level L: $d^L = v^k$
Optical vector flow estimation for subsequent level: $g^{L-1} = 2(g^L + d^L)$
End of cycle on L
Final optical flow vector: $d = g^0 + d^0$
Final result q (position of the representative point in the context of image B):

$$q = p + d$$

c2) Motion Estimation Module with the Block Matching Method

This option can be appropriate and/or preferable in the presence of sequences with limited time support or with particularly significant noise levels where the differential methods may be difficult to estimate, and in the specific embodiment proposed below it is able to use or integrate the optical flow information deriving from the application of methods of the region-based type. This type of approach defines the optical flow vector as the displacement that guarantees the greatest similarity between image regions at different time points. The term similarity is formalized through cross-correlation functions or by minimizing difference functions. This method also has advantages in the degree of scalability in terms of computational complexity. In this second embodiment, the algorithm described in the publication [2] cited above (block matching type solution with hexagonal search model) is taken as the basic reference. An embodiment of the method implemented and subsequently adapted to the type of images processed, and therefore specifically optimized in the context of the present invention, is articulated through the following steps.

In terms of pseudo-code, the algorithm can be represented according to the following steps.

If p is a representative point in the context of image A, find the corresponding position q in the context of image B.

Construction of a multi-resolution pyramidal representation of images A and B:

$A:\{A^L\}_{L=0 \ldots L_n} B:\{B^L\}_{L=0 \ldots L_n}$

Initialization of initial estimation relative to the minimum resolution level $g^{L_m}=[g_x^{L_m}, g_y^{L_m}]=[0,0]$ Proceed from $L=L_m$ up to $L=0$ with step 1:

Position of the point p on image $A^L: p^L = p/2^L$

Actual search start position: $p_s = p^L + g^L$

The following matching criterion being defined:

$$MAD = \frac{1}{n^2} \sum_{y=p_y-r_y}^{p_y+r_y} \sum_{x=p_x-r_x}^{p_x+r_x} |I_t(x, y) - I_{t+1}(x + dx, y + dy)|$$

Figure 6:
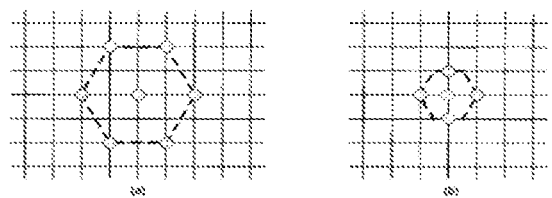
FIG. 6 illustrates the patterns used for an HBM (Hexagonal Block Matching) type search according to an implementation technique that can be used in the invention.

Start search procedure using hexagonal pattern (FIG. 6). The search is carried out by applying the above-mentioned criterion in a block with the dimension $(2 \times r+1) \times (2 \times r+1)$ centred in $p_s$. The algorithm is constrained to a suitable search window sized in such a way as to include all the possible admissible displacements. At the first step, the larger hexagonal model with seven control points is used to start the search. If the matching criterion is minimal in the central point, the search is refined by using the second model with four search points. If the matching criterion is minimal in one of the peripheral points, the search is continued using the large model. The various steps are summarized and formalized below:

Step 1) The larger hexagonal model is placed in the centre of the search window. The matching criterion MAD is applied at each of the seven points of the pattern in question. If the minimum point is the central one, proceed to Step 3), otherwise to Step 2).

Step 2) Three new search points are added along the side containing the minimum point. In this way a new large hexagonal model is formed which is centred in the current minimum and contains the four points evaluated in the previous step plus the three new ones. The criterion MAD is applied to the latter: if the minimum is at the centre of the new model or the search window limit has been reached, continue with Step 3), otherwise continue with Step 2).

Step 3) The model is changed by switching to the smaller hexagonal pattern. The matching criterion is evaluated for each of the four points introduced and is compared with the minimum found in the previous step. The displacement vector $g^L=(\widetilde{dx}^L, \widetilde{dy}^L)$ of the block relative to the minimum MAD resulting from this comparison will be the solution sought in the context of this level.

If L=0 the cycle ends, otherwise it continues with an estimation of the optical flow vector for the next level: $g^{L-1}=2g^L$ End of cycle on L Final optical flow vector: $g=g^0$ Final result q (position of the representative point in the context of image B):

$q=p+g$ c3) Motion Estimation Module with the Phase Information Based Method

A mathematical treatment and the subsequent translation into pseudo-code for the implementation of a method that follows this approach can be directly derived from the publication [3] cited above and to which reference is made.

Downstream of the estimation module, again in a practical embodiment of the invention, a classification module d) is provided as mentioned above, within which analytical operations of the axial components of the motions are carried out. These axial components are in fact considered discriminatory for the purpose of identifying the mirror artifacts. The following operations are implemented within the module.

Rejection of anomalous estimations: the level of reliability of the estimation deriving from the application of the single estimation module c1), c2) or c3) is evaluated in terms of norm of the optical flow vector, if this value is higher than a plausible threshold value with the displacements allowed in the specific context, meaning that for that given representative point, the single method has encountered convergence problems with the desired solution. If the specific implementation involves the simultaneous use of several motion estimation modules, it is possible to use result filtering or voting strategies to guarantee a sufficient level of anomaly rejection and improve the overall robustness of the calculation model.

Classification and refinement through spatial uniformity constraints: while the individual estimation modules of the optical flows described above exploit the principle of motion uniformity limited to an area of radius r associated with the representative point, the subsequent operations act by analysing the motion uniformity between neighbouring representative points. Within this module, the following operations are advantageously carried out:

1. Identification of elements with non-null axial motions: exploiting the optical flow information, individual image regions are classified according to the direction of the corresponding axial component. This operation produces a ternary graph containing the three motion classes considered: motion with axial direction facing upwards, motion with axial direction facing downwards and motion with null axial direction.

Figure 7:
FIG. 7 is a mask image for classifying the real component before the refinement operations, with the elements associated with image regions with upward axial movements (real image portion)
Figure 9:
FIG. 9 is a mask image for classifying the mirror component before the refinement operations, with the elements associated with image regions with downward axial movements (mirror image portion)

2. Classification of representative points associated with real and mirror image elements: the purpose of this operation is to identify the direction relative to the mirror components. By integrating the information deriving from the ternary graph, the occurrences are analysed based on the sign of the axial component of the optical flow vectors. The direction with the least number of occurrences defines the direction of the mirror components; this hypothesis is valid until there are more real image elements than the elements caused by artifacts. During this phase it is assumed that the distribution of the various estimation errors (outliers) has a null average and therefore does not influence the classification itself. Alternative solutions for specific acquisition methods envisage performing the calculations of occurrences in predetermined regions for which a lower presence of mirror components is assumed. At the end of this operation the two binary graphs are produced, one for each component (FIG. 7, FIG. 9).

3. Filtering isolated elements from binary images: in each of the previous graphs the non-null elements for which there are no neighbouring elements belonging to the same class are removed. These elements represent isolated representative points for which a non-null optical flow vector has been estimated and most likely caused by the presence of structured noise such as speckle noise. The term "removal" means that the components of the optical flow vector for the representative point in question are set to a null value.

Figure 8:
FIG. 8 is a mask image for classifying the real component after the refining operations.
Figure 10:
FIG. 10 is a mask image for classifying the mirror component after the refining operations.

4. Application of morphological operators on filtered binary images: the purpose of these operations is to apply, where necessary, the spatial motion uniformity constraint through morphological operators such as closure and region filling inside the graphs. The results of these operations are shown respectively in FIG. 8, FIG. 10.

Lastly, the reconstruction module e) is reached, with which the individual mirror components present in the tomographic image are identified using the classification provided by the previous module. In particular, the following operations are carried out:

1. Overturning the image regions belonging to representative points classified as mirror artifact: starting from the graph relative to the real signal, the corresponding image regions are identified. These regions are transposed in a mirror-like manner within an area created starting from a wider extension of the real image itself.

2. Removal and replacement of regions containing mirror artifacts: the image regions belonging to representative points classified as mirror artifact are removed and replaced with regions containing an artificial noise pattern generated while respecting the distribution parameters characterizing the speckle noise present in the real image itself.

Figure 11:
FIG. 11 is a tomographic image containing the final result produced by a reconstruction module according to the invention.

The final result produced by the artifact removal module is shown in FIG. 11, from which the quality and cleanliness of the image available to the operator can be appreciated.

It will also be understood that with the system and method conceptually configured according to the above description, the detection quality and speed go hand in hand with marked prerogatives of structural simplicity (the result being achieved with digital editing techniques and without resorting to accessory components). The system is also flexible, in particular making it possible to adapt the estimation module used according to the limitations or in any case to the circumstances of use defined in the contour, and can be integrated with multi-resolution strategies aimed at pushing the accuracy of the result to the highest levels.

The present invention has been described herein with reference to preferred embodiments. It is to be understood that there may be other embodiments that relate to the same inventive concept within the scope of protection defined by the appended claims.

The invention claimed is:

1. An optical coherence tomography system comprising: a broadband light radiation source; a reference optical arm; movable scanning means for scanning a sample, adapted to receive light radiation emitted by said source to illuminate a portion of the sample corresponding to a position of the scanning means, generating a radiation hitting a surface of the sample, and collecting backscattered radiation from the sample; a signal detection arm with a sensor adapted to reconstruct a signal spectrum resulting from the radiation collected by said reference arm and by said scanning means; beam splitter means adapted to permit the passage of the radiation from the source to the scanning means and to the reference arm, and from these to the detection arm; and a control and processing unit configured to transform said spectrum in a reflectivity profile of the illuminated sample portion, and to generate an image of the sample by juxtaposing a number of reflectivity profiles each corresponding to a portion of the sample and a displacement of said scanning means; wherein said control unit is further configured to obtain a time sequence of images of the sample, and to execute processing steps of an optical flow obtained from said sequence, said processing steps comprising: motion estimations of graphic features of the images between two or more consecutive images; based on said estimations, classification of said features by distinction between mirror artifact graphic features and real graphic features; and reconstruction of a final image of the sample to remove said mirror artifact graphic features.

2. The apparatus according to claim 1, wherein said classification is executed on the basis of differences in components of axial motion between said mirror artifact graphic features and said real graphic features, obtained with said motion estimations.

3. The apparatus according to claim 1, wherein said motion estimations are conducted starting from a resolution of the optical flow represented by a linear equation system obtained by imposing a motion uniformity condition in a neighborhood of a point under consideration.

4. The apparatus according to claim 1, wherein said motion estimations are conducted by subdividing the images of the sample in blocks and carrying out similarity measurements among the blocks within the time sequence of images, wherein said similarity measurements are maximized inside a given searched spatial window.

5. The apparatus according to claim 1, wherein said motion estimations are conducted with methods based on characteristics of motion vectors in a transform domain.

6. The apparatus according to claim 1, wherein said motion estimations are conducted with pixel based recursive methods.

7. The apparatus according to claim 1, wherein said motion estimations are conducted with a combination of one or more methods.

8. The apparatus according to claim 1, wherein said control unit is further configured to carry out filtering operations, before said processing steps, adapted to increase a signal to noise ratio in said images of the sample.

9. The apparatus according to claim 1, wherein said classification comprises: rejection of anomalous estimations by comparison with a predetermined normal value of an optical flow vector; identification of features with non-null axial motions and said classification based on a direction of a corresponding axial component with creation of a ternary graph containing three motion classes of high, low, null; identification of the direction relative to said mirror artifact graphic features integrating data obtained from said ternary graph; filtering isolated elements from binary graphs, by removing non-null elements for which there are no close elements belonging to the same class; and application of morphologic operators on the filtered binary graphs.

10. The apparatus according to claim 9, wherein said reconstruction comprises: overturning image regions belonging to representative points classified as said mirror artifact graphic features in a graph of a real image; mirror-like displacement of said image regions inside an area created by starting from a wider extension than the real image; removing the regions containing said mirror artifact graphic features and replacing them with regions containing an artificial noise pattern generated by respecting the distribution parameters characterizing the speckle noise in the real image.

* * * * *